US007393929B1

(12) United States Patent
Debyser et al.

(10) Patent No.: US 7,393,929 B1
(45) Date of Patent: Jul. 1, 2008

(54) INHIBITORS OF CELLULOLYTIC, XYLANOLYTIC AND β-GLUCANOLYTIC ENZYMES

(75) Inventors: Winok Debyser, Grimbergen (BE); Jan Delcour, Heverlee (BE)

(73) Assignee: Danisco A/S, Kobenhaven (DK)

( * ) Notice: Subject to any disclaimer, the term of this patent is extended or adjusted under 35 U.S.C. 154(b) by 0 days.

(21) Appl. No.: 09/403,625

(22) PCT Filed: May 4, 1998

(86) PCT No.: PCT/EP98/02590

§ 371 (c)(1),
(2), (4) Date: Feb. 7, 2000

(87) PCT Pub. No.: WO98/49278

PCT Pub. Date: Nov. 5, 1998

(30) Foreign Application Priority Data

Apr. 30, 1997 (EP) .................................. 97870060

(51) Int. Cl.
*A61K 36/00* (2006.01)
*C07K 1/00* (2006.01)
*C12N 9/00* (2006.01)
*C12N 9/44* (2006.01)
*C12N 5/00* (2006.01)

(52) U.S. Cl. .................. 530/375; 435/183; 435/200; 435/201; 435/410; 530/350; 530/370

(58) Field of Classification Search .................. 530/350, 530/370, 375, 374; 435/183, 200, 201, 410
See application file for complete search history.

(56) References Cited

U.S. PATENT DOCUMENTS

| 6,265,201 B1 | 7/2001 | Wackett et al. |
| 6,267,956 B1 | 7/2001 | Gomes et al. |
| 6,277,612 B1 | 8/2001 | Golightly et al. |

FOREIGN PATENT DOCUMENTS

| EP | 0 979 830 | 2/2000 |
| WO | WO 96/29416 | 9/1996 |
| WO | WO 98/05788 | 2/1998 |
| WO | WO 98/49278 | 5/1998 |
| WO | WO 00/39289 | 7/2000 |
| WO | WO 01/98474 | 12/2001 |

OTHER PUBLICATIONS

Ham et al. Fungal pathogens secrete an inhibitor protein that distinguishes isoforms of plant pathogenesis-related endo-.beta.-1,3-glucanases. Plant J., Feb. 1997, vol. 11(2), pp. 169-179.*
Jones et al. A protein inhibitor of cellulases in Dictyostelium discoideum. Biochem Biophys Res Commun. Oct. 30, 1981, vol. 102, pp. 1310-1316.*
Proteins : Structures and Molecular Properties, 2nd ed., Thomas E. Creighton, p. 4, Table 1.1.*
Proteins : Structures and Molecular Properties, 2nd ed., 1940, Thomas E. Creighton, p. 4, Table 1.1.*
Lothar Ziser et al., Syntheses and testing of substrates and mechanism-based inactivators for xylanases, *Carbohydrate Research*, vol. 247, 1995, pp. 137-153.
Sulabha S. Keskar et al., Characterization and sequencing of an active-site cysteine-containing peptide from the xylanase of a thermotolerant Streptomyces, *Biochem. Journal*, vol. 281, 1992, pp. 601-605.
D.J. Gomes et al., Factors influencing the induction of endo-xylanase by *Thermoascus aurantiacus*, Journal of Biotechnology, vol. 33, 1994, pp. 87-94.
Jaishree Paul et al., Influence of Sugars on Endoglucanase and β-Xylanase Activities of a Bacillus Strain, *Microbiology Unit, School of Life Sciences*, 1990, pp. 61-64.
Winok Debyser et al., Arabinoxylan Solubilization and Inhibition of the Barley Malt Xylanolytic System by Wheat During Mashing with Wheat Wholemeal Adjunct: Evidence for a New Class of Enzyme Inhibitors in Wheat, *J. Am. Soc. Brew. Chem.*, vol. 55(4), 1997, pp. 153-156.
Tracey D. Spurway et al. *Calcium Protects a Mesophilic Xylanase from Proteinase Inactivation and Thermal Unfolding*, www.jbc.org, 1993, pp. 17523-17530.
Ziser, Lothar et al: "Syntheses and testing of substrates and mechanism-based inactivators for xylanases", Carbohydr. Res. (1995), 274, 137-53.
Keskar, Sulabha S. et al: "Characterization and sequencing of an active-site cysteine-containing peptide from the xylanase of a thermotolerant streptomyces", Biochem. J. (1992), 281(3), 601-5.
Gomes, D. J. et al: "Factors influencing the induction of endoxylanase by *Thermoascus aurantiacus*", J. Biotechnol. (1994), 33(1), 87-94.
Paul, Jaishree et al: "Influence of sugars on endoglucanase and.beta.-xylanase activities of a Bacilus strain", Biotechnol. lett. (1990), 12(1), 61-4.
Debyser, Winok et al: "Arabinoxylan solubilization of the barley malt xylanolytic system by wheat during mashing with wheat wholemeal adjunct: evidence for a new class of enzyme inhibitors in wheat", J. Am. Soc. Brew. Chem. (1997), 55(4), 153-156.
Spurway, Tracey D. et al: "Calcium protects a mesophilic xylanase from proteinase inactivation and thermal unfolding", J. Biol. Chem. (1997), 272(28).
Chapter IV from Gebruers, K. et al., 2002 PhD. Thesis.
Fierens, K., et al: Molecular identification of wheat endoxylanase inhibitor TAXI-I[1], member of a new class of plant proteins, FEBS Letters 540 (2003) 259-263.
Chapter III from Goesaert, H. et al., 2002 PhD Thesis.

(Continued)

*Primary Examiner*—Tekchand Saidha
*Assistant Examiner*—Christian L. Fronda
(74) *Attorney, Agent, or Firm*—Nixon & Vanderhye P.C.

(57) ABSTRACT

The present invention concerns an inhibitor of xylanolytic and/or β-glucanolytic enzymes, method for obtaining the inhibitor, said inhibitor and processes for obtaining micro-organism, plant or plant material wherein the activity of the inhibitor according to the invention is increased or reduced and to the use of the inhibitor, the cited micro-organism, plant or plant material in a variety of processes and applications.

1 Claim, 1 Drawing Sheet

OTHER PUBLICATIONS

Figure 1:
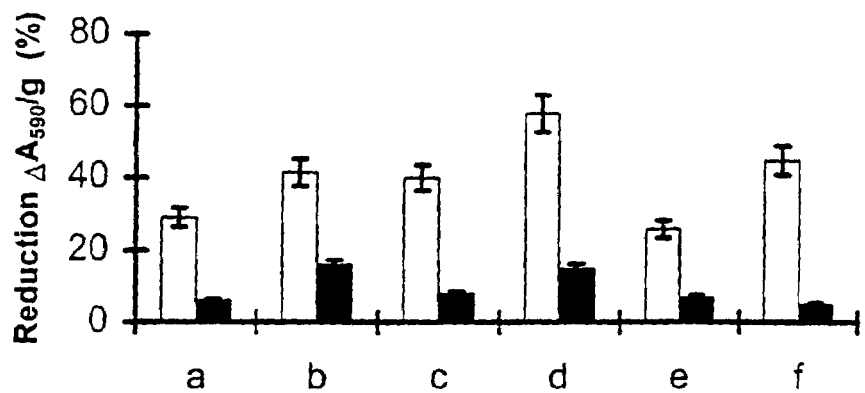

Gebruers, K. et al: "Properties of TAXI-type endoxylanase inhibitors", Biochimica et Biophysica Acta 1696 (2004), 213-221.

Bailey, et al., "Production of xylanases by *Aspergillus fumigatus* and *Aspergillus oryzae* on xylan-based media", World Journal of Microbiology and Biotechnology, vol. 9, 1993.

McLauchlan, et al., "A Novel class of protein from wheat which inhibits xylanases[1]", Biochem. J. (1999) 338, 441-446.

Debyser, et al., "Triticum aestivum Xylanase Inhibitor (TAXI), a New Class of Enzyme Inhibitor Affecting Breadmaking Performance", Journal of Cereal Science 30 (1999) 39-43.

Gebruers, et al., "Triticum aestivum L. endoxylanase inhibitor (TAXI) consists of two inhibitors, TAXI I and TAXI II, with different specificities", Biochem. J. (2001) 353, 239-244.

Goesaert, et al., "Purification and Partial Characterization of an Endoxylanase Inhibitor from Barley", American Association of Cereal Chemists, Inc., vol. 78, No. 4, 2001.

Bernalier et al "Inhibition of the cellulolytic activity of *Neocallimastix frontalis* by *Ruminococcus flavefaciens*", Journal of General Microbiology (1993), 139, 873-880.

Mes-Hartree et al "The nature of inhibitory materials present in pretreated lignocellulosic substrates which inhibit the enzymatic hydrolysis of cellulose", Biotechnology Letters, vol. 5, No. 8, 531-536.

Translation of Japanese Office Action/Notice of Reason for Rejection mailed Oct. 24, 2006, issued in connection with Japanese Patent Application No. 546621/98.

Mes-Hartree et al "The nature of inhibitory materials present in pretreated lignocellulosic substrates which inhibit the enzymatic hydrolysis of cellulose", Biotechnology Letters, vol. 5, No. 8, 531-536 (1983).

\* cited by examiner

INHIBITORS OF CELLULOLYTIC, XYLANOLYTIC AND β-GLUCANOLYTIC ENZYMES

This is the U.S. national phase under 35 U.S.C. § 371 of International Application PCT/EP98/02590, filed May 4, 1998.

FIELD OF THE INVENTION

This invention relates to an inhibitor of cellulolytic, xylanolytic and/or β-glucanolytic enzymes (sometimes also referred to as cellulases, pentosanases and/or hemicellulases) especially an inhibitor of pentosan degrading enzymes such as endoxylanase (such as EC: 3.2.1.8), β-xylosidase (such as EC: 3.2.1.37), and α-L-arabinofuranosidase (such as EC: 3.2.1.55), to inhibitors of cellulase (such as EC: 3.2.1.4), β-glucanase (such as EC: 3.2.3.73 or EC: 3.2.1.6), and to inhibitors of other xylan, arabinoxylan and β-glucan degrading enzymes, which are present in micro-organisms, plants, plant materials or fractions thereof, (such as cereals, cereal grains, cereal flours or fractions thereof).

The present invention is also related to a method for obtaining said inhibitor, as well as to the use of said inhibitor in different areas of food, feed and/or beverage technologies, such as malting and brewing, the production of animal feedstuffs such as to increase their conversion, the production of baked and/or extruded cereal products such as straight dough, sponge and dough and Chorleywood breads, breakfast cereals, different types of biscuits, pasta and noodles, the production of starch derived syrups, sorbitol, xylose and/or xylitol, the wheat gluten-starch separation industry, maize processing, the improvement of plant disease resistance, in nutraceutical or pharmaceutical applications such as maintaining the structure of dietary fiber material, and in the field of paper and pulp technologies.

BACKGROUND OF THE INVENTION

Apart from barley malt, unmalted cereals such as wheat are commonly used in beer production (Pierce, J. S., *Proceedings of the European Brewery Convention Congress*, Madrid, 1987, 445). Unmalted wheat (40-50%) is e.g. used for the production of Belgian white (wheat) beers.

Although barley and wheat endosperm cell walls contain 20 and 70% (w/w) arabinoxylan respectively (Ballance, G. M., & Manners, D. J., *Carbohydrate Research*, 1978, 61, 107; Fincher, G. B., & Stone, B. A. In: *Advances in Cereal Science and Technology*, Vol. VIII. Y. Pomeranz, (Ed), Am. Assoc. Cereal Chem., St. Paul (MN), 1986, 207), their total arabinoxylan content is comparable, i.e. 2.8 to 7.1% (w/w) for barley and 3.6 to 7.1% (w/w) for wheat (Henry, J., *Journal of the Science of Food and Agriculture*, 1985, 36, 1243; Hashimoto, S., Shogren, M. D. & Pomeranz, Y., *Cereal Chemistry*, 1987, 64, 30).

The grains also contain comparable levels of water-extractable arabinoxylan, i.e. 0.24 to 0.80% (w/w) for barley and 0.25 to 1.18% for wheat (Henry, J., *Journal of the Science of Food and Agriculture*, 1985, 36, 1243; Hashimoto, S., Shogren, M. D. & Pomeranz, Y., *Cereal Chemistry*, 1987, 64, 30; Aman, P., & Hesselman, K., *Swedish Journal of Agricultural Research*, 1984, 14, 135; Girhammer, U., & Nair, B. M., *Food Hydrocolloids*, 1992, 6, 285). Furthermore, barley and wheat endosperm cell walls contain 70 and 20% β-glucan respectively (Ballance, G. M., & Manners, D. J., *Carbohydrate Research*, 1978, 61, 107; Fincher, G. B., & Stone, B. A. In: *Advances in Cereal Sciences and Technology*, Vol. VIII. Y. Pomeranz, (Ed), Am. Assoc. Cereal Chem., St. Paul (MN), 1986, 207).

Barley grains contain 1.7 to 4.1% (w/w) water-extractable and 3.6 to 6.4% (w/w) total β-glucan (Anderson, M. A., Cook, J. A., & Stone, B. A., *Journal of the Institute of Brewing*, 1978, 84, 233-239; Henry, J., *Journal of the Science of Food and Agriculture*, 1985, 36, 1243). Wheat grains contain 0.1 to 0.8% (w/w) water-extractable and 0.6 to 1.4% (w/w) total β-glucan (Anderson, M. A., Cook, J. A., & Stone, B. A., *Journal of the Institute of Brewing*, 1978, 84, 233-239; Henry, J., *Journal of the Science of Food and Agriculture*, 1985, 36, 1243). As in wheat only low levels of arabinoxylan (Cleemput, G., Bleukx, W., van Oort, M., Hessing, M. & Delcour, J. A., *Journal of Cereal Science*, 1995, 22, 139) and β-glucan degrading enzyme activities can be measured, the barley malt must be mostly responsible for wheat and malt arabinoxylan and β-glucan hydrolysis during brewing.

Efficient hydrolysis of arabinoxylans and β-glucan is important because such compounds can be involved in production problems such as wort viscosity (Ducroo, P. & Frelon, P. G., *Proceedings of the European Brewery Convention Congress*, Zurich, 1989, 445; Viëtor, R. J. & Voragen, A. G. J., *Journal of the Institute of Brewing*, 1993, 99, 243) and filterability and haze formation (Coote, N. & Kirsop, B. H. 1976., *Journal of the Institute of Brewing*, 1976, 82, 34; Izawa, M., Kano, Y. & Kanimura, M. 1991. *Proceedings Aviemore Conference on Malting, Brewing and Distilling*, 1990, 427).

In other areas efficient hydrolysis of xylans and/or arabinoxylans is highly desirable as well. Examples include rye and wheat breadmaking processes, paper and pulp technologies. It follows that a lot of research efforts have been devoted to the (potential) applications of xylan and/or arabinoxylan hydrolysis enzymes due to their applications as described above.

SUMMARY OF THE INVENTION

The present invention concerns an inhibitor of cellulolytic, xylanolytic and/or β-glucanolytic enzymes, preferably an inhibitor of endoxylanase, of β-glucanase, of β-xylosidase, of α-L-arabinofuranosidase, and of other xylan, arabinoxylan and β-glucan degrading enzymes preferably obtained from micro-organisms, plants, plant materials or fractions thereof (such as cereals, cereal grains, cereal germs or fractions thereof, cereal flours or fractions thereof).

"An inhibitor of an enzyme" means a molecule which is able to inhibit partially or totally the activity of said enzyme. In irreversible inhibition, the inhibitor is covalently linked to the enzyme or bound so tightly that its dissociation from the enzyme is very slow. In this case, the inhibitor usually mimics the normal substrate of said enzyme in a cross-linking reaction. In contrast, reversible inhibition may be characterised by a rapid equilibrium between the enzyme and the inhibitor. A competitive inhibitor prevents the substrate from binding to the active site and may reduce the reaction rate by diminishing the proportion of enzyme molecules that are bound to substrate. In non-competitive inhibition, the inhibitor may decrease the turnover number. Competitive inhibition can be distinguished from non-competitive inhibition by determining whether the inhibition can be overcome by raising the substrate concentration. Inhibitors isolated from a specific biological species and that are of proteinaceous or glycoproteinaceous nature can be active against enzymes of the same species (i.e. endogeneous enzymes) and/or against enzymes of different species (i.e. exogeneous enzymes).

Advantageously the inhibitor of the invention can be produced by micro-organisms or may be present in various extraction media from micro-organisms or plant material, such as cereals or fractions thereof, such as cereal grains or fractions thereof, such as cereal germs or fractions thereof, such as cereal flours or fractions thereof, such as from wheat, durum wheat, rye, triticale, barley, sorghum, oats, maize and/or rice, from which it can be obtained by the methods well knows by the person skilled in the art. According to a preferred embodiment of the present invention, the inhibitor is a xylanase inhibitor which is typically water-soluble alkaline proteinaceous species, having a pI (i.e.—log of the isoelectric point) of greater than about 7.0. The xylanase inhibitor molecular weight as determined by SDS-page is typically 40-43 kDa. Following reduction with β-mertaptoethanol three SDS-page protein bands are found with SDS-page molecular weights of ca. 40-43 kDa, ca. 30 kDa, and ca. 10 kDa. The N-terminal sequence of the 40-43 kDa protein or glycoprotein has not been described until now and is typically as follows: SEQ ID No. 1: Lys-Gly-Leu-Pro-Val-Leu-Ala-Pro-Val-Thr-Lys-Xaa-Thr-Ala, wherein Xaa being preferably Asp. The 30 kDa band has the above described typical N-terminal amino acid SEQ ID NO:1, while the N-terminal amino acid sequence of the 10 kDa band is typically as follows: SEQ ID No.2: Gly-Ala-Pro-Val-Ala-Arg-Ala-Val-Ile-Pro-Val-Ala-Pro-Phe-Glu-Leu-Xaa, wherein the Xaa is unidentified. This sequence has not been described before.

Therefore, the present invention is also related to an inhibitor with an SDS-page molecular weight of typically 40-43 kDa being a protein or glycoprotein having a marker whose amino acid sequence has more than 70% homology, preferably more than 85% homology, more preferably is identical with SEQ ID No. 1.

The present invention is furthermore also related to an inhibitor with an SDS-page molecular weight of typically 30 kDa being a protein or glycoprotein having a marker whose amino acid sequence has more than 70% homology, preferably more than 85% homology, more preferably is identical with SEQ ID No. 1.

The present invention is furthermore also related to an inhibitor with an SDS-page molecular weight of typically 10 kDa being a protein or glycoprotein having a marker whose amino acid sequence has more than 70% homology, preferably more than 85% homology, more preferably is identical with SEQ ID No. 2.

Advantageously, said markers are the end-terminal amino acid sequences of the protein or glycoprotein.

According to the invention, a marker of a protein or glycoprotein means a specific amino acid sequence (or its corresponding nucleotide acid sequence) that is able to distinguish one protein family from another protein family.

The inhibitory effect towards xylan and/or arabinoxylan hydrolysing enzymes can be e.g. demonstrated by the endoxylanase method with AZCL arabinoxylan (cfr. infra). Likewise, the inhibitory effect towards β-glucan hydrolysing enzymes can be e.g. demonstrated by the β-glucanase method with AZCL β-glucan (cfr. infra).

The invention also relates to a method for obtaining said inhibitor from a micro-organism, such as a genetically modified micro-organism which expresses said inhibitors, from a plant, or from a plant material such as cereals, cereal grains, cereal flours or fractions thereof), by subjecting said plant, said plant material and/or said micro-organism to one or more extraction and/or fractionation steps.

Another aspect of the present invention is related to a method for genetically transforming a micro-organism, a plant or a plant material in order to obtain the expression of the inhibitor according to the invention wherein the micro-organism, the plant or plant material is genetically modified by the introduction of a genetic material encoding said inhibitor into the micro-organism, the plant or plant material and obtain its translation and expression by genetic engineering methods well known by the man skilled in the art.

The invention furthermore relates to processes aiming at changing, preferably reducing or increasing level of said inhibitor in a micro-organism, a plant or a plant material, by reducing or increasing the expression of said inhibitor, by the methods well known by the man skilled in the art and/or by using molecules which are able to block the inhibitor activity or activate said inhibitor.

The invention furthermore relates to the obtained inhibitor, micro-organism, plant, plant material, and/or fractions thereof and to their use in different areas of food, feed and/or beverage technologies, such as improving malting and brewing, improving animal feedstuffs efficiency, baked and/or extruded cereal products (such as straight dough, sponge and dough and Chorleywood breads, breakfast cereals, different types of biscuits, pasta and noodles), improving the production of starch derived syrups, sorbitol, xylose and/or xylitol, improving wheat gluten-starch separation and production, maize processing, improving plant disease resistance, improving nutraceutical or pharmaceutical applications (such as maintaining the structure of dietary fiber material), and improving paper and pulp technologies.

The present invention will be described in details in the following description of a preferred embodiment without limiting the scope of the present invention.

DETAILED DESCRIPTION OF THE INVENTION

During the course of their work dealing with the structure of arabinoxylans in Belgian white beers and in intermediates in the production process, the inventors unexpectedly found indications for inhibition of the xylanolytic barley malt system by wheat water extractables. This has not been reported before, although it has clearly been established that endogenous and exogenous (α-amylase (Deponte, R., Parlamenti, T., Petrucci, V., Silano, V., & Tomasi, M., *Cereal Chemistry*, 1976, 53, 805; Buonocore, V., Petrucci, T., & Silano, V., *Phytochemistry*, 1977, 16, 811; Mundy, J., Hejgaard, J., & Svendsen, I., *Federation of Societies*, 1984, 167, 210; Silano, V. α-Amylase inhibitors. In: *Enzymes and their Role in Cereal Technology*, J. E. Kruger, D. Lineback and C. E. Stauffer, (Eds). Am. Assoc. Cereal Chem., St. Paul (MN), 1987, 141) and protease (Birk, Y., *Methods Enzymology*, 1976, 45, 723; Lawszkowski, M., & Kato, I., *Annual Review of Biochemistry*, 1980, 49, 593) inhibitors are present in cereal grains.

Indeed, when one measured the solubilization of arabinoxylans during brewing with barley malt and unmalted wheat, with the objectives (1) to relate enzymic activities of the starting materials with the arabinoxylan contents of corresponding worts, and (2) to investigate in which way wheat interferes with the solubilization of arabinoxylans during brewing, there was evidence for the presence of xylanase inhibitors in wheat. This was indeed observed when one compared the solubilization of arabinoxylans and the release of free xylose (Xyl) in wort prepared with 60% malt and 40% wheat with that in a 100% malt wort.

Under certain experimental conditions, the addition to the wort of a xylanase of microbial origin clearly improved arabinoxylan solubilization during wort preparation.

EXAMPLES

Materials

β-D-Allose, β-mercaptoethanol, p-nitro-phenyl-β-D-xylopyranoside and Trizma base (reagent grade, tris[hydroxymethyl]amino-methane) were obtained from Sigma, St-Louis, Mo., USA. Azurine-crosslinked (AZCL) wheat arabinoxylan (Xylazyme arabinoxylan tablets), AZCL and Xylanase M4 from *Aspergillus niger* was from Megazyme, Bray, Ireland. Microbial xylanases from the micro-organisms *Bacillus substilis, Trichoderma viride* and *Aspergillus niger* were obtained from NV Puratos, Groot-Bijgaarden, Belgium. Buffer A was: 0.025 M sodium acetate, pH 4.7; Buffer B was: 0.025 M sodium maleate, pH 6.0; Buffer C was: 0.025 M sodium phosphate pH 6.0; Buffer D was: 0.250 mM sodium acetate pH 5.0; Buffer E was: 0.025 M sodium acetate pH 5.0.

Barley malt samples were supplied by Cargill Malt Division, Herent (Belgium). The inventors used a two-rowed winter barley variety (Clarine) with a low endoxylanase activity and low water-extractable Xyl content, and two malts from a six-rowed winter barley variety Plaisant, with a high water-extractable Xyl content. Plaisant malt samples 1 and 2 had high and low endoxylanase activities respectively. Wheat samples were from Amylum, Aalst (Belgium) and SAPSA SES SA, Jodoigne (Belgium). The inventors used Skirlou and Soissons with high and low water-extractable Xyl contents, respectively. Wheat germs were supplied by Ceres, Vilvoorde (Belgium). Rye flour was from a mixture of Dutch rye varieties supplied by Meneba, Rotterdam (The Netherlands). Barley from the variety Clarine was supplied by Cargill, Malt Division, Herent (Belgium). Clarine barley, Plaisant 1 and Plaisant 2 barley malts, Skirlou and Soissons wheat wholemeals were prepared either with the Tecator sample mill (Höganäs, Sweden) or for the brewing experiments with an EBC-approved laboratory mill (Analytica-EBC, Fourth edition, Brauerei-und Getränke-Rundschau, Zurich, 1987). Soissons wheat flour was produced with a Büahler MLU-202 laboratory mill (Bühler, Uzwil, Switzerland, extraction yield 70%).

Extracts

BMWM1 WWM, and WG

Samples (3.00 g) of ground barley malt and wheat or wheat germ (1.00 g) were suspended in buffer A (10.0 mL). After 15 min of vigorous shaking at room temperature, the suspensions were centrifuged (3,000 g, 15 min, 20° C.). The resulting extracts are referred to as BMWM1 (barley malt wholemeal extract 1), WWM (wheat wholemeal extract), and WG (wheat germ extract).

WF, RF, and BWM

Samples of the appropriate flour or wholemeal (2.50 g) were suspended in buffer B (10.0 mL). After 15 min of vigorous shaking at room temperature, the suspensions were centrifuged (10,000 g, 15 min, 20° C.) and the supernatants were filtered (0.45µ) The resulting wholemeal extracts are referred to as WF (wheat flour extract), RF (rye flour extract), and BWM (barley wholemeal extract).

BMWM2

Samples (5.00 g) of ground barley malt were suspended in buffer B (10.0 mL). After 15 min of vigorous shaking at room temperature, the suspensions were centrifuged (10,000 g, 15 min, 20° C.) and the supernatants were filtered (0.45µ). The resulting wholemeal extracts are referred to as BMWM2 (barley malt wholemeal extract 2).

Methods

Determination of Xyl content

Extraction and hydrolysis procedures were as described by Cleemput et al (Cleemput, G., Roels, S. P., van Oort, M., Grobet P. J. & Delcour, J. A., *Cereal Chemistry*, 1993, 70, 324), with heating (130° C.) of samples of whole meal (wheat and barley malt) for 5 hours to eliminate enzyme activity prior to extraction. Worts were analysed in the same way as the water-extracts of the whole meal flours. Free Xyl was determined by omitting the hydrolysis step prior to alditol acetate preparation. Alditol acetate samples (1 µl) (Englyst, H. N. & Cummings J. H., *Analyst*, 1984, 109, 937) were separated at 225° C. on a Supelco SP-2380 column (30 m, 0.32 mm ID, 0.2 µm film thickness) and detected with a flame ionisation detector in a Chrompack 9011 Chromatograph (Middelburg, The Netherlands). Injection and detection temperatures were 275° C. β-D-Allose was used as internal standard. The arabinose (Ara) measured originated from both arabinoxylan and arabinogalactan making it impossible to calculate arabinoxylan levels as 0.88×(Ara+Xyl) (Cleemput, G., van Oort, M., Hessing, M., Bergmans, M. E. F., Gruppen, H., Grobet, P. J., Delcour, J. A., *Journal of Cereal Science*, 1995, 22, 73-84). Moreover, as in water-extracts of wheat wholemeal a substantial part of the galactose (Gal) does not stem from arabinogalactan, correction of Ara figures for arabinogalactan by assuming that the Gal/Ara ratio in arabinogalactan is 1.5 as known for wheat flours (Izydorczyk, M., Biliaderis, C. G. & Bushuk, W., *Cereal Chemistry*, 1991, 68, 139-144) was equally impossible. In what follows, therefore, the Xyl figures are used as a relative measure for arabinoxylans levels. In a similar way, the increase in Xyl levels during brewing is indicative of arabinoxylan solubilization during brewing.

Measurement of Endoxylanase (EC 3.2.1.8) Activity and Inhibition Thereof

Extracts (1.0 mL) BMWM1 and WWM (cfr. supra) were incubated for 5 min at 50° C., before adding an AZCL-xylan tablet (Megazyme). The incubation was then continued for 60 min at 50° C. The reaction was terminated by adding 1% (w/v) Trizma base (10.0 mL) and vigorous vortex stirring. After 5 min at room temperature, the tubes were shaken vigorously and the contents filtered through a Whatman No 1 filter. The absorbance was measured at 590 nm against a control, which was prepared by incubating the extract without the substrate tablet for 60 min at 50° C. The substrate tablet was added after adding 1% (w/v) Trizma base to the extract. The activity was expressed as the difference in the absorbance at 590 nm between the sample and control and expressed per gram dry malt ($\Delta A_{590}/g$).

The endoxylanase activity of 0.6 mL BMWM1 (cfr. supra) and 0.4 mL buffer A was compared with the activity of 0.6 mL BMWM1 to which 0.4 mL WWM was added. In some cases, the WWM was boiled for 30 min and centrifuged (3,000 g, 15 min, 20° C.) prior to addition.

In the evaluation of the inhibition of microbial enzymes by extracts from different cereals the following procedure was used. Extracts (WF, WG, RF, and BWM) or boiled (30 min, 100° C.) and centrifuged (10,000 g, 15 min, 20° C.) extracts (250 µL) were preincubated for 30 min at room temperature with 250 µL of appropriately diluted microbial xylanase solution, the xylazyme tablet was added and the mixture was incubated for 60 min at 50° C. The remainder of the procedure was as described above with addition of 5.0 mL 2% (w/v) Trizma base instead of 10.0 mL 1% (w/v) to terminate the reaction.

Measurement of β-Glucanase (EC: 3.2.3.73) Activity and Inhibition Thereof.

Extracts (WF, RF, and BWM) or boiled (30 min, 100° C.) and centrifuged (10,000 g, 15 min, 20° C.) extracts (450 µL) were preincubated for 30 min at room temperature with 50 µL of BMWM2, the β-glucazyme tablet was added and the mixture was incubated for 60 min at 40° C. The remainder of the procedure was as described above with addition of 5.0 mL 2% (w/v) Trizma base instead of 10.0 mL 1% (w/v) to terminate the reaction.

Brewing

Worts were prepared in duplicate according to the EBC method (Analytica-EBC, Fourth edition, Brauerei-und Getränke-Rundschau, Zurich, 1987). For the 100% barley malt worts, 50.0 g barley malt was used and for the worts with 40% wheat, 30.0 g barley malt and 20.0 g wheat. Worts were centrifuged for 15 min at 2,000×g (room temperature). The spent grains were washed (150 mL) and the washings were added to the worts.

The *Bacillus subtilis* endoxylanase was added to the water (46° C.) before mixing with 60% Clarine malt and 40% Soissons or Skirlou wheat. The level of endoxylanase added to worts (0.867 $\Delta A_{590}$/g) was equal to that needed to increase the endoxylanase activity of Clarine malt (0.750 $\Delta A_{590}$/g) to the level in Plaisant 1 malt (1.617 $\Delta A_{590}$/g).

All analyses described above were carried out at least in duplicate and the mean values are presented. The experimental error (E.E.) was calculated from the difference (in %) between the individual and the mean values.

SDS-Polyacrylamide Gel Electrophoresis and Iso-Electrofocusing

The molecular weight of the purified inhibitor was determined by SDS-polyacrylamide gel electrophoresis (SDS-page) on 20% polyacrylamide gels under reducing (β-mercaptoethanol, 1%) or non-reducing conditions with the PhastSystem unit (Pharmacia, Uppsala, Sweden), according to the method of Laemmli, U.K. (*Nature*, 1970, 227, 680-685). The gels were silver stained according to the instructions of the manufacturer (Pharmacia, Development Technique file NO 210). Low molecular weight markers were α-lactalbumin (14,400 Da); trypsin inhibitor (20,100 Da); carbonic anhydrase (30,000 Da); ovalbumin (43,000 Da); albumin (67,000 Da); phosphorylase b (94,000 Da). The isoelectric point of the inhibitor was determined with the PhastSystem unit using polyacrylamide gels containing ampholytes (pH 3-9) and with appropriate standards (Pharmacia calibration kits, pI 3.5-9.3) The proteins were silver stained (cfr. supra).

N-Terminal Amino Acid Sequencing of Proteins.

The sequences of the N-terminal amino acids were determined with an Applied Biosystems model 477 A gas-phase sequencer, connected on line with an 120 A PTH analyser (Perkin Elmer, Belgium).

Evidence for the Presence of Endoxylanase Inhibitors in Wheat

Barley malt and wheat Xyl levels and arabinoxylan hydrolysing activities are listed in Table I. Xyl levels in the 100% malt worts (Table II) varied from 0.41 to 0.62% (all analytical data expressed as percentage of dry matter). The Xyl levels in the warts with 40% wheat varied from 0.35 to 0.61% (Table III).

In the worts with 40% wheat, the inventors used 60% barley malt. Comparison of the increase in Xyl during brewing using 60% malt with 60% of the Xyl increase using 100% barley malt showed a reduction of 12 to 58% (Tables II and III). This suggested that the endoxylanases from barley malt were inhibited in the presence of wheat or that the wheat arabinoxylans are a less suitable substrate for malt endoxylanases. Malting breaks down barley cell walls and renders them more accessible for enzymes (Selvig, A., & Aarnes, H., *Journal of the Institute of Brewing*, 1986, 92, 185).

Free Xyl Levels in Wort

The levels of free Xyl in 100% malt warts varied from 0.046 to 0.076% and in the warts with 40% wheat from 0.025 to 0.040% (Table IV). The difference between the levels of the released free Xyl was 0.032 to 0.044% for the 100% malt worts and 0.015 to 0.020% for the worts with 40% wheat. The reduction in free Xyl release compared with 60% of the free Xyl release with the 100% barley malt wart varied from 1 to 32% (Tables II and IV). The use of the *Bacillus subtilis* endoxylanase did not result in an increase of free Xyl. The free Ara levels did also not increase. The endoxylanase, therefore, had no side β-D-xylosidase and α-L-arabinofuranosidase activities.

The reduction of the endoxylanase induced increase in Xyl or arabinoxylan solubilization as a result of the use of wheat in conjunction with barley malt was more obvious than the reduction of the release of free Xyl. For this reason one focused on the inhibition of the barley malt endoxylanases by a wheat component.

Malt Xylanolytic System Inhibition by Wheat Extracts

In FIG. 1 the reduction of the endoxylanase activity of BMWM1, when WWM instead of buffer A was added, is given. The reduction of endoxylanase activity varied from 26 to 58%. The reduction of endoxylanase activity of barley malt wholemeal extracts (BMWM1) was obtained by addition of wheat wholemeal extracts (WWM) instead of buffer. The FIG. 1 represents the results obtained with unboiled (□) and boiled extracts (■). (a) Clarine malt+Soissons wheat, (b) Clarine malt+Skirlou wheat, (c) Plaisant 1 malt+Soissons wheat, (d) Plaisant 1 malt+Skirlou wheat, (e) Plaisant 2 malt+Soissons wheat, (f) Plaisant 2 malt+Skirlou wheat.

A higher reduction was observed in case of cv. Skirlou than with cv. Soissons. This was in line with the higher reduction of Xyl increase during brewing with cv. Skirlou than with cv. Soissons (see Table III). The higher water extractable Xyl content of cv. Skirlou than for cv. Soissons implied that the lower susceptibility of the wheat substrate during brewing may cause the reduced solubilization. When boiling WWM, almost all of the inhibition disappeared. The inhibitor seemed to be thermolabile and the inventors concluded that it therefore may be of proteic nature. However, it was considered unlikely that one dealt with a protease as the protease activity from the malt is many times higher than the protease activity of wheat. The major part of the reduced activity was apparently not caused by the wheat arabinoxylans because the thermal treatment did not change the arabinoxylan concentration of the wheat extract. Whether the wheat inhibitor was active against the endogenous barley malt endoxylanases or exogenous endoxylanases was unclear.

Figure 2:
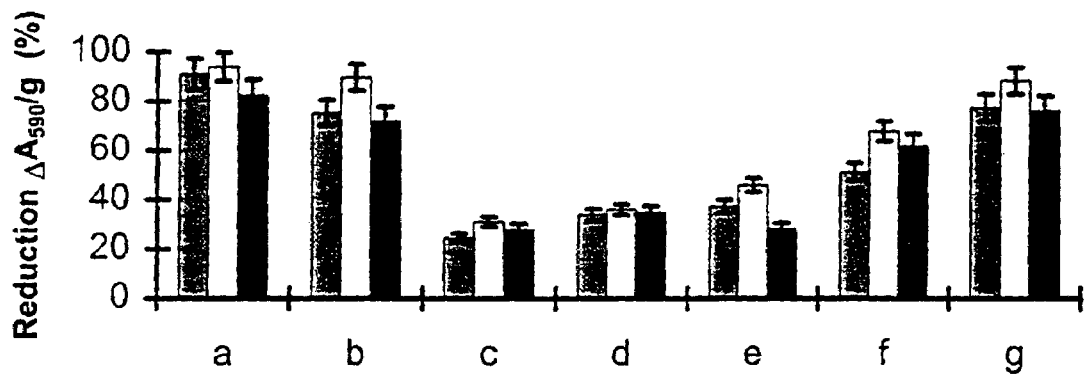

Brewing with *Bacillus subtilis* Xylanase: a Solution for Poor Arabinoxylan Solubilisation in Barley Malt—Wheat Wholemeal Brewing The *Bacillus subtilis* endoxylanase, one of the microbial enzymes that was relatively little inhibited under the experimental conditions of FIG. 2, increased the Xyl levels present in wort. In comparison with the same worts made without endoxylanase addition, 94% more Xyl solubilization using cv. Soissons as wheat adjunct and 179% more Xyl solubilization using cv. Skirlou as wheat adjunct was obtained. The

*Bacillus subtilis* endoxylanase apparently solubilizes more arabinoxylan from the wheat variety Skirlou than from the wheat variety Soissons (Table IV).

Purification of Xylanase Inhibitor from Wheat Flour

Soissons wheat flour (2.0 kg) was suspended in 10.0 L 0.1% (w/v) ascorbic acid. The suspension was mixed overnight at 7° C. and centrifuged (7° C., 10,000 g, 30 min). To the supernatant 2.0 g/l $CaCl_2$ was added and the pH was raised to 9.0 by addition of 2.0 M NaOH. The extract was left overnight at 7° C. and centrifuged (7° C., 10,000 g, 30 min). The pH of the extract was adjusted to 5.0 with 2.0 M HCl and the extract was pumped over a cation exchanger (SP Sepharose Fast Flow, 50×50 mm, Pharmacia). The column was equilibrated with buffer C (200 mL) and a protein fraction was eluted with 200 mL 0.5 M NaCl. This eluate was diluted 5 times, the pH adjusted to 5.0 as above and cations were exchanged (SP Sepharose Fast Flow, 26×100 mm, Pharmacia). The column was equilibrated with buffer C (200 mL) and after a linear salt gradient from 0 to 0.5 M NaCl (800 mL), fractions of 10 mL were, after desalting (PD 10 column, Pharmacia), assayed for endoxylanase inhibition using the cited xylazyme method with eluate instead of cereal extract and appropriately diluted Xylanase M4 from *Aspergillus niger*. The fractions with inhibition activity were collected, dialyzed against dionised water (7° C., overnight) and lyophilised. The lyophilised material was dissolved in buffer D (6.0 mL) and separated on a Sephacryl S100 column (26×670 mm, Pharmacia) eluted with the same buffer. Fractions of 2.5 mL were collected and assayed for inhibitor activity. The active fractions were collected, dialyzed as above and lyophilised. The lyophilised material was dissolved in buffer E (6 mL) and cation exchanged (Mono S HR 5/5, Pharmacia) with the same buffer. Fractions eluted in a salt gradient (0 to 0.5 M NaCl) were collected and assayed for xylanase inhibition as above. In this way, we obtained a fraction (1 mL) of the inhibitor which migrated as a single protein band on SDS-PAGE. it had an apparent molecular weight of ca. 40-43 kDa. Following reduction with β-mercaptoethanol, two additional SDS-PAGE bands of molecular weights of typically 30 and 10 kDa are detected.

N-Terminal Amino Acid Sequencing of Endoxylanase Inhibitor

The β-mercaptoethanol reduced inhibitor protein and/or glycoprotein fractions were subjected to SDS-page, blotted and N-terminal amino acid sequenced.

The N-terminal amino acid sequence of the ca. 40-43 kDa band (SEQ ID No. 01) was: Lys-Gly-Leu-Pro-Val-Leu-Ala-Pro-Val-Thr-Lys-Xaa-Thr-Ala wherein Xaa being preferably Asp. This sequence has not been reported before. The above cited ca. 30 kDa band also has the above described typical N-terminal amino acid SEQ ID No.1, while the N-terminal amino acid sequence of the ca. 10 kDa band is typically as follows: SEQ ID No.2: Gly-Ala-Pro-Val-Ala-Arg-Ala-Val-Ile-Pro-Val-Ala-Pro-Phe-Glu-Leu-Xaa, wherein the Xaa is unidentified. This sequence has not been described before.

Inhibition of Different Microbial Endoxylanases by Endoxylanase Inhibitors from Wheat and Other Cereals In FIG. 2 the inhibition of different microbial xylanases in the presence of WF, RF, and BWM is shown. The reduction of the xylanase activity (%) when a cereal extract was added instead of the same extract boiled for 30 min is given. Under the experimental conditions, the highest reduction was found for the mixture of three xylanases from *Trichoderma reesei* (82 to 94%) the lowest for the xylanases from *Bacillus subtilis* (24 to 39%).

The reduction of microbial endoxylanase activity was obtained by addition of cereal extracts (WF, RF, and BWM) instead of boiled cereal extracts. The FIG. 2 represents the results obtained with wheat flour (■), rye flour (□) and barley whole meal (■). Microbial xylanases: (a) Mixture of three xylanases from *Trichoderma reesei*, (b) Xylanase M4 from *Aspergillus niger*, (c) Xylanase from *Bacillus subtilis*, (d) Mixture of three xylanases from *Bacillus subtilis*, (e) Xylanase from *Aspergillus niger*, (f) Mixture of five xylanases from *Aspergillus niger*, (g) Mixture of five xylanases from *Aspergillus niger*. Under the experimental conditions, WG reduced the activity of xylanase M4 from *Aspergillus niger* with ca. 80%.

Figure 3:
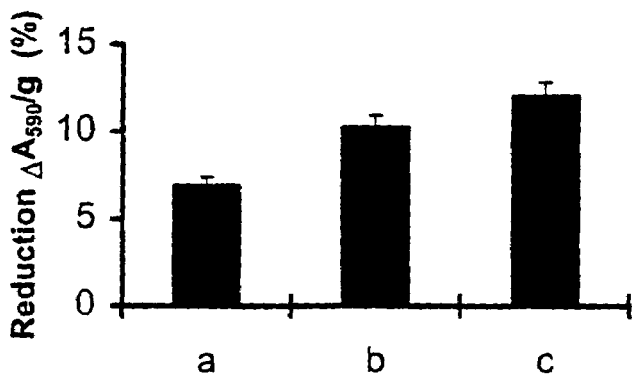

Inhibition of Barley Malt β-Glucanase by Inhibitors from Wheat and Other Cereals In FIG. 3 the inhibition of malt β-glucanase in the presence of WF, RF, and BWM is shown. The reduction of the β-glucanase activity (%) when a cereal extract was added instead of the same extract boiled for 30 min is given. The reduction varied from 7 to 12%.

The reduction of β-glucanase activity of barley malt extracts (BMWM2) was obtained by addition of cereal extracts (WF, RF, BWM) instead of boiled cereal extracts. The FIG. 3 represents the results obtained with wheat flour (a), rye flour (b) and barley whole meal (c).

TABLE I

Water-extractible and Free Xylose Contents (% of Dry Matter) and Arabinoxylan Degrading Enzyme Activities of 3 Barley Malts and 2 Wheats*.

| | Water-extractable Xyl | Free Xyl | Endoxylanase ($\Delta A_{590}$/g) | β-D-Xylosidase (U/g) |
|---|---|---|---|---|
| Barley Malt | | | | |
| Clarine | 0.29 | 0.014 | 0.750 | 0.286 |
| Plaisant 1 | 0.41 | 0.031 | 1.617 | 0.331 |
| Plaisant 2 | 0.40 | 0.013 | 0.607 | 0.299 |
| Wheat | | | | |
| Soissons | 0.27 | 0.005 | 0.115 | 0.054 |
| Skirlou | 0.52 | 0.003 | 0.205 | 0.053 |
| | E.E. < 7% | E.E. < 4% | E.E. < 9% | E.E. < 6% |

*Xyl = xylose;
Water-extractable Xyl = total − free xylose water-extract;
E.E. = experimental error.

TABLE II

Xylose and Free Xylose Levels (% of Dry Matter) in Wort and Levels of Increase in Xylose and Free Xylose (% of Dry Matter) during Brewing with 100% Barley Malt*.

| Barley Malt | Xyl Wort | Xyl Increase | Free Xyl Wort | Free Xyl Increase |
|---|---|---|---|---|
| Clarine | 0.41 | 0.15 | 0.046 | 0.032 |
| Plaisant 1 | 0.62 | 0.26 | 0.075 | 0.044 |
| Plaisant 2 | 0.51 | 0.09 | 0.049 | 0.035 |
| | E.E. < 6% | | E.E. < 7% | |

*Xyl = xylose;
Xyl Wort = total − free xylose wort;
Xyl Increase = total xylose wort − total xylose water-extract barley malt;
Ara = arabinose;
E.E. = experimental error.

TABLE III

Xylose Levels (% of Dry Matter) in Grains and Corresponding Worts Prepared with 60% Barley Malt and 40% Wheat. Increase in Xylose Levels (% of Dry Matter) during Brewing and Effect of Addition of *Bacillus subtilis* Endoxylanase. Difference (%) with 60% of the Increase of Xylose Levels in Case of a 100% Malt Wort*.

| Barley Malt (60%) + Wheat (40%) | Xyl Grains | Xyl Wort | Xyl Increase | Difference 100% Malt Wort |
|---|---|---|---|---|
| Clarine + Soissons | 0.29 | 0.35 | 0.08 | −12 |
| Clarine + Skirlou | 0.41 | 0.46 | 0.07 | −27 |
| Plaisant 1 + Soissons | 0.35 | 0.44 | 0.10 | −36 |
| Plaisant 1 + Skirlou | 0.48 | 0.53 | 0.06 | −58 |
| Plaisant 2 + Soissons | 0.35 | 0.39 | 0.06 | −28 |
| Plaisant 2 + Skirlou | 0.48 | 0.51 | 0.05 | −40 |
| Clarine + Soissons + BSX | 0.31 | 0.45 | 0.16 | 93 |
| Clarine + Skirlou + BSX | 0.44 | 0.61 | 0.19 | 130 |
|  | E.E < 8% | E.E. < 7% |  |  |

*Xyl = xylose;
Xyl Grains = 0.6 × (total − free xylose water-extract barley malt) + 0.4 × (total − free xylose water-extract wheat);
Xyl wort = total − free xylose wort;
Xyl Increase = total xylose wort − [0.6 × (total xylose water-extract barley malt) + 0.4 × (total xylose water-extract wheat)];
Difference 100% Malt Wort = [100 × (increase xylose wort from 60% malt and 40% wheat)/(xylose increase wort from 100% malt)] − 100;
BSX = *Bacillus subtilis* endoxylanase;
E.E. = experimental error.

TABLE IV

Release of Free Xylose during Brewing with 60% Barley Malt and 40% Wheat. Effect of Addition of *Bacillus subtilis* Endoxylanase. Difference (%) with 60% of the Release of Xylose in Case of a 100% Malt Wort*.

| Barley Malt (60%) + Wheat (40%) | Free Xyl | | | |
|---|---|---|---|---|
|  | Grains | Wort | Release | Difference 100% Malt Wort |
| Clarine + Soissons | 0.010 | 0.025 | 0.015 | −20 |
| Clarine + Skirlou | 0.010 | 0.029 | 0.019 | −1 |
| Plaisant 1 + Soissons | 0.021 | 0.039 | 0.018 | −32 |
| Plaisant 1 + Skirlou | 0.020 | 0.040 | 0.020 | −24 |
| Plaisant 2 + Soissons | 0.010 | 0.029 | 0.019 | −9 |
| Plaisant 2 + Skirlou | 0.009 | 0.029 | 0.020 | −5 |
| Clarine + Soissons + BSX | 0.010 | 0.026 | 0.015 | −19 |
| Clarine + Skirlou + BSX | 0.010 | 0.029 | 0.019 | −2 |
|  | E.E. < 8% | E.E. < 7% |  |  |

*Xyl = xylose;
Difference 100% Malt Wort = [100 × (xylose release wort from 60% malt and 40% wheat)/(xylose release wort from 100% malt)] − 100;
BSX = *Bacillus subtilis* endoxylanase;
E.E. = experimental error.

What is claimed is:

1. An isolated wheat protein or glycoprotein inhibitor of xylanase, which inhibitor is a water-soluble, alkaline protein or glycoprotein, which protein or glycoprotein inhibitor has a pI of greater than about 7.0 and a molecular weight of about 40-43 kDa as measured by SDS-PAGE, said inhibitor resolving as two separate bands on SDS-PAGE after reduction with β-mercaptoethanol, said two separate bands having molecular weights of about 30 kDa and about 10 kDa said protein or glycoprotein comprises the amino acid sequence of SEQ ID NO:1 and said two separate bands comprise the amino acid sequences of SEQ ID NO:1 and SEQ ID NO:2, respectively.

* * * * *

SEQUENCE LISTING

```
<160> NUMBER OF SEQ ID NOS: 2

<210> SEQ ID NO 1
<211> LENGTH: 14
<212> TYPE: PRT
<213> ORGANISM: wheat
<220> FEATURE:
<221> NAME/KEY: UNSURE
<222> LOCATION: (12)
<223> OTHER INFORMATION: preferably Asp

<400> SEQUENCE: 1

Lys Gly Leu Pro Val Leu Ala Pro Val Thr Lys Xaa Thr Ala
 1               5                  10

<210> SEQ ID NO 2
<211> LENGTH: 17
<212> TYPE: PRT
<213> ORGANISM: wheat
<220> FEATURE:
<221> NAME/KEY: UNSURE
<222> LOCATION: (17)
<223> OTHER INFORMATION: unidentified

<400> SEQUENCE: 2

Gly Ala Pro Val Ala Arg Ala Val Ile Pro Val Ala Pro Phe Glu Leu
 1               5                  10                  15

Xaa
```